(12) United States Patent
Jan et al.

(10) Patent No.: US 9,200,948 B2
(45) Date of Patent: Dec. 1, 2015

(54) TOMOGRAPHIC SCANNING APPARATUS

(71) Applicant: INSTITUTE OF NUCLEAR ENERGY RESEARCH, ATOMIC ENERGY COUNCIL, EXECUTIVE YUAN, Taoyuan County (TW)

(72) Inventors: Meei-Ling Jan, Longtan Township (TW); Tien-Hsiu Tsai, Longtan Township (TW); Ho-Hui Hsieh, Longtan Township (TW)

(73) Assignee: INSTITUTE OF NUCLEAR ENERGY RESEARCH, ATOMIC ENERGY COUNCIL, EXECUTIVE YUAN (TW)

( * ) Notice: Subject to any disclaimer, the term of this patent is extended or adjusted under 35 U.S.C. 154(b) by 6 days.

(21) Appl. No.: 14/329,059

(22) Filed: Jul. 11, 2014

(65) Prior Publication Data

US 2015/0115143 A1    Apr. 30, 2015

(30) Foreign Application Priority Data

Oct. 28, 2013   (TW) .............................. 102138976 A

(51) Int. Cl.
*A61B 6/00*     (2006.01)
*G01J 1/02*     (2006.01)
*A61B 6/03*     (2006.01)
*G01N 23/04*    (2006.01)

(52) U.S. Cl.
CPC ............... *G01J 1/0223* (2013.01); *A61B 6/035* (2013.01); *G01N 23/046* (2013.01); *G01N 2223/308* (2013.01); *G01N 2223/3303* (2013.01)

(58) Field of Classification Search
CPC ........ A61B 6/03; A61B 6/035; A61B 6/4476; G01N 21/01
USPC ................... 250/221, 234, 236, 358.1, 360.1, 250/363.02; 378/11, 12, 13
See application file for complete search history.

(56) References Cited

U.S. PATENT DOCUMENTS

2015/0117597 A1*   4/2015   Jan ......................... A61B 6/035
                                                               378/20

* cited by examiner

*Primary Examiner* — Kevin Pyo
(74) *Attorney, Agent, or Firm* — Schmeiser, Olsen & Watts, LLP

(57) ABSTRACT

A tomographic scanning apparatus for scanning an object under test and retrieving projection-related data of the object with a light/radiation source and a detector operating in conjunction therewith includes an object carrier, a light/radiation source carrier, a detector carrier, a control module, a processing module, and a rail system (or rotating arm). The object carrier is disposed at a center of the rail system or a center of rotating tracks of the rotating arm. The light/radiation source carrier and the detector carrier move along a rail of the rail system or along the rotating tracks of the rotating arm. The carriers have a rotating mechanism, moving mechanism, and/or height adjusting mechanism for performing rotation, horizontal movement, and/or height adjustment. Accordingly, the tomographic scanning apparatus operates in various ways to suit various applications, respectively.

19 Claims, 8 Drawing Sheets

TOMOGRAPHIC SCANNING APPARATUS

CROSS-REFERENCE TO RELATED APPLICATION

This non-provisional application claims priority under 35 U.S.C. §119(a) on Patent Application No(s). 102138976 filed in Taiwan, R.O.C. on Oct. 28, 2013, the entire contents of which are hereby incorporated by reference.

FIELD OF THE TECHNOLOGY

The present invention relates to tomographic scanning apparatuses, particularly to a tomographic scanning apparatus for scanning an object under test and retrieving projection-related data of the object under test from different angles of view, and more particularly to a tomographic scanning apparatus capable of scanning in various modes.

BACKGROUND

Tomographic scanning is a non-invasive imaging technology for examining internal structures of creatures (in animal research, veterinary medicine, and medical diagnosis) and lifeless objects (in industrial screening technology), hereinafter referred to as objects under test. A conventional tomographic scanning apparatus is typically equipped with a light/radiation source (which emits X-ray, gamma ray, visible light beams, or laser light beams, for example) and a detector. Tomographic scanning entails scanning an object under test with the light/radiation source, retrieving projection-related data of the object under test from different angles of view, performing image computation and reconstruction, and eventually identifying how constituent elements of the object under test are distributed therein (that is, producing sectional images of the object under test.)

The operation and dedicated movement mechanism of a conventional tomographic scanning apparatus are designed to meet a single need. That is to say, a specific tomographic scanning apparatus is characterized by its specific scanning operation and its specific purpose, thereby resulting in specialization of tomographic scanning apparatuses. Hence, there are commercially available special tomographic scanning apparatuses, such as dental tomographic scanning apparatuses, mammo-tomographic scanning apparatuses, vertical thoracic synthesized tomography scanning apparatuses, and industrial noninvasive tomographic scanning apparatuses. As a result, once the hardware mechanisms of the tomographic scanning apparatuses are designed and put into production, they can only perform scanning in the specific mode only. To suit a change in application, a wide-ranging change or re-design of the hardware mechanisms of the tomographic scanning apparatuses is possible, albeit incurring a discouragingly huge amount of costs.

SUMMARY

In view of the aforesaid drawbacks of the prior art, it is an objective of the present invention to provide a tomographic scanning apparatus for performing scanning in various modes by various motion mechanisms, so as to augment the flexibility of the application of tomographic scanning apparatuses and cut the costs incurred in modifying and/or redesigning the mechanisms of tomographic scanning apparatuses.

In order to achieve the above and other objectives, the present invention provides a tomographic scanning apparatus, having a light/radiation source for scanning an object under test and a detector for retrieving projection-related data of the object under test, comprising: a rail system lying on a reference plane; an object carrier adapted to carry the object under test and disposed at a center of the rail system; a light/radiation source carrier adapted to carry the light/radiation source, movably disposed at the rail system, and comprising a rotating mechanism and a moving mechanism, the rotating mechanism driving the light/radiation source to rotate about an axis of the light/radiation source carrier, the axis being perpendicular to the reference plane, and the moving mechanism driving the light/radiation source to undergo translation across the reference plane or across a plane parallel to the reference plane; a detector carrier adapted to carry the detector, movably disposed at the rail system, and comprising a rotating mechanism and a moving mechanism, the rotating mechanism driving the detector to rotate about an axis of the detector carrier, and the moving mechanism driving the detector to undergo translation across the reference plane or across a plane parallel to the reference plane; a control module having signal communication with the light/radiation source carrier and the detector carrier to control operation of the light/radiation source carrier and the detector carrier according to a pre-configured scanning mode, thereby allowing the light/radiation source to irradiate the object under test according to the pre-configured scanning mode, and allowing the detector to retrieve projection-related data of the object under test according to the pre-configured scanning mode; and a processing module having signal communication with the detector to access the projection-related data retrieved by the detector.

In an embodiment, the rail system comprises a closed rail. The light/radiation source carrier and the detector carrier are movably disposed at the closed rail. The closed rail is a circular path or an elliptical path.

In an embodiment, the rail system comprises a first closed rail and a second closed rail enclosing the first closed rail. The light/radiation source carrier is disposed at one of the first and second closed rails, and the detector carrier is disposed at another one of the first and second closed rails.

In order to achieve the above and other objectives, the present invention further provides another tomographic scanning apparatus, having a light/radiation source for scanning an object under test and a detector for retrieving projection-related data of the object under test, comprising: an object carrier lying on a reference plane and adapted to carry the object under test; a first rotating arm comprising a first carrying mechanism and a first rotating mechanism, wherein the first rotating mechanism is disposed at an end of the first rotating arm, the object carrier is mounted on the first rotating mechanism, the first rotating mechanism drives the first rotating arm to rotate about an axis of the object carrier, the axis being perpendicular to the reference plane, and the first carrying mechanism is disposed at another end of the first rotating arm; a second rotating arm comprising a second carrying mechanism and a second rotating mechanism, the second carrying mechanism being disposed at an end of the second rotating arm, and the second rotating mechanism being disposed at another end of the second rotating arm and rotating about the axis of the object carrier; a light/radiation source carrier adapted to carry the light/radiation source, disposed at the first carrying mechanism of the first rotating arm, and comprising a rotating mechanism and a moving mechanism, the rotating mechanism driving the light/radiation source to rotate about an axis of the light/radiation source carrier, and the moving mechanism driving the light/radiation source to undergo translation across one of the reference plane and a plane parallel to the reference plane; a detector carrier adapted to carry the detector, disposed at the second carrying mechanism of the second rotating arm, and comprising a rotating mechanism and a moving mechanism, the rotating mechanism driving the detector to rotate about an axis of the detector carrier, and the moving mechanism driving the detector to undergo translation across one of the reference plane and a plane parallel to the reference plane; a control module having signal communication with the light/radiation source carrier, the detector carrier, the first rotating arm, and the second rotating arm to control the light/radiation source carrier, the detector carrier, the first rotating arm, and the second rotating arm according to a pre-configured scanning mode and thus allow the object under test to be irradiated by the light/radiation source according to the pre-configured scanning mode and allow the detector to retrieve the projection-related data of the object under test according to the pre-configured scanning mode; and a processing module having signal communication with the detector to access the projection-related data retrieved by the detector.

In an embodiment, the first rotating arm and the second rotating arm are of equal lengths. In another embodiment, the first rotating arm and the second rotating arm are of different lengths.

In an embodiment, the object carrier has signal communication with the control module, and the object carrier includes a rotating mechanism for driving the object under test to rotate about the axis of the object carrier.

In an embodiment, the object carrier has signal communication with the control module, the object carrier includes a height adjusting mechanism whereby the object under test undergoes height adjustment in a height adjustment direction parallel to an axis of the object carrier, the light/radiation source carrier includes a height adjusting mechanism whereby the light/radiation source undergoes height adjustment in a height adjustment direction parallel to an axis of the light/radiation source carrier, and/or the detector carrier includes a height adjusting mechanism whereby the detector undergoes height adjustment in a height adjustment direction parallel to an axis of the detector carrier.

Accordingly, the tomographic scanning apparatus of the present invention is characterized in that an object carrier, a light/radiation source carrier and a detector carrier each include a rotating mechanism, a moving mechanism and a height adjusting mechanism for controlling the object carrier, the light/radiation source carrier and the detector carrier in moving along a rail system which operates in conjunction with two rotating arms, To carry out multiple scanning modes and meet all possible scanning needs, it is preferably that the object carrier, the light/radiation source carrier, and the detector carrier each comprise a height adjusting mechanism.

BRIEF DESCRIPTION OF THE DRAWINGS

Objectives, features, and advantages of the present invention are hereunder illustrated with specific embodiments in conjunction with the accompanying drawings, in which.

DETAILED DESCRIPTION OF THE PREFERRED EMBODIMENTS

Figure 1:
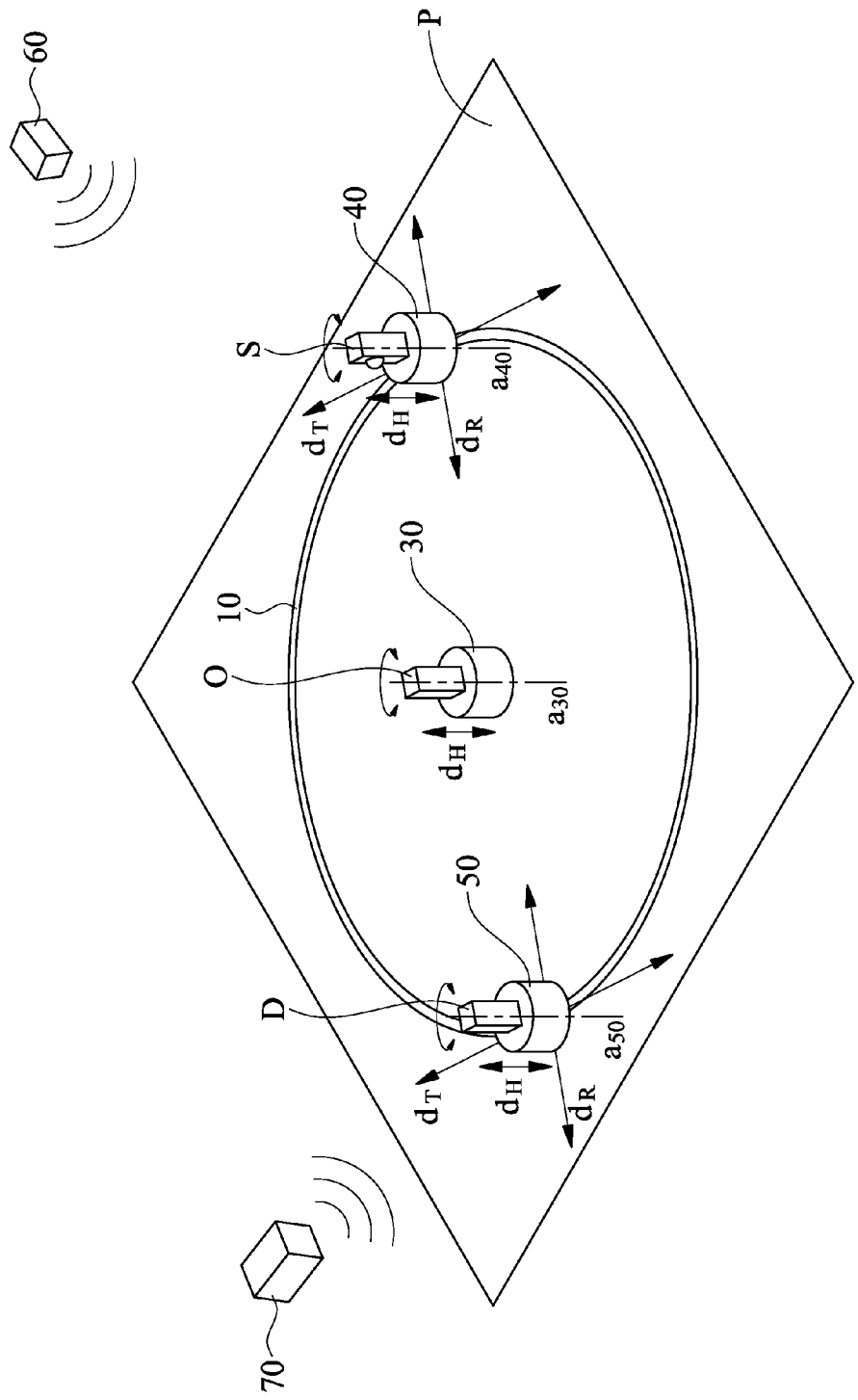
FIG. 1 is a schematic view of a tomographic scanning apparatus according to the first embodiment of the present invention.
Figure 2A:
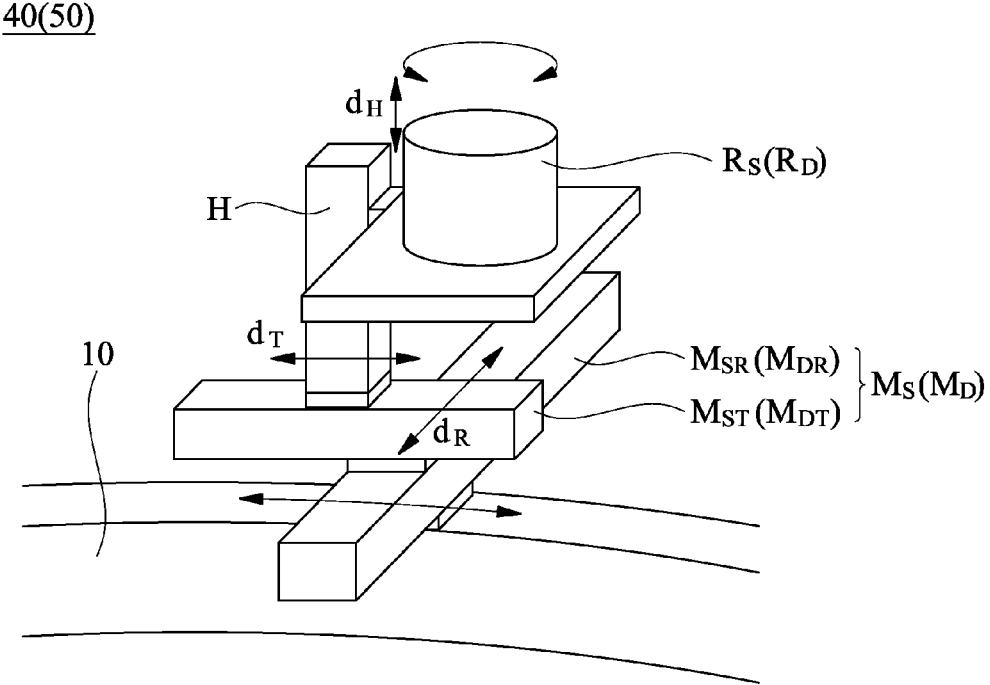
FIG. 2A is a schematic view of a light/radiation source carrier or a detector carrier of the tomographic scanning apparatus shown in FIG. 1.
Figure 2B:
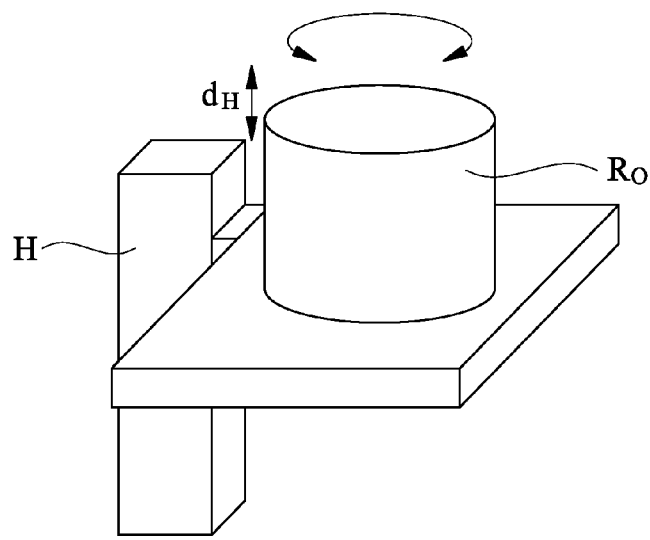
FIG. 2B is a schematic view of an object carrier of the tomographic scanning apparatus shown in FIG. 1.

Referring to FIG. 1, FIG. 2A, and FIG. 2B, there are shown in FIG. 1 a schematic view of a tomographic scanning apparatus 1 according to the first embodiment of the present invention, in FIG. 2A a schematic view of a light/radiation source carrier or a detector carrier of the tomographic scanning apparatus, and in FIG. 2B a schematic view of an object carrier of the tomographic scanning apparatus. The tomographic scanning apparatus 1 is equipped with a light/radiation source S for scanning an object under test O and a detector D for retrieving projection-related data of the object under test O, wherein the light/radiation source S emits an X-ray, a gamma ray, a visible light beam, or a laser beam. The tomographic scanning apparatus 1 comprises a rail system 10, an object carrier 30, a light/radiation source carrier 40, a detector carrier 50, a control module 60, and a processing module 70.

The rail system 10 lies on a reference plane P. In the first embodiment, the rail system 10 comprises a closed rail. The closed rail preferably follows a circular path or an elliptical path, but the present invention is not limited thereto. In a variant embodiment, the rail system 10 comprises an opened rail (not shown), such as a C-shaped rail or a notched closed rail. A main purpose of the rail system 10 is to transport the light/radiation source carrier 40 and the detector carrier 50; hence, the rail system 10 can include a sliding rail, and a toothed structure (not shown) is disposed on the outer or inner side of the sliding rail and adapted to guide the toothed carriers in motion, for example, but the rail system 10 is not limited thereto. Regardless of its form, the rail system 10 of the present invention will work, provided that it is capable of guiding the carriers in the manner as described above.

The object carrier 30 carries the object under test O. The object carrier 30 is disposed at the center of the rail system 10 and thus surrounded by the rail system 10. The object carrier 30 has signal communication with the control module 60. The object carrier 30 comprises a rotating mechanism $R_O$. The rotating mechanism $R_O$ of the object carrier 30 is controlled by the control module 60 having signal communication with the object carrier 30, and is adapted to drive the object carrier 30 to rotate about an axis $a_{30}$ thereof under the control of the control module 60. The axis $a_{30}$ of the object carrier 30 is perpendicular to the reference plane P. In this embodiment, the ultimate purpose of the rotating mechanism $R_O$ of the object carrier 30 is to effect the rotation of the object under test O about the axis $a_{30}$.

The rotating mechanism $R_O$ is provided in the form of a direct drive motor for driving the object under test O to rotate, but the present invention is not limited thereto. Regardless of its form, the rotating mechanism $R_O$ will work, provided that it drives the object under test O to rotate.

The light/radiation source carrier 40 carries the light/radiation source S and is movably disposed at the rail system 10. The movement of the light/radiation source carrier 40 can be effectuated, because, for example, the light/radiation source carrier 40 comprises a power source and a transmission device (not shown) for driving a gear. The gear meshes with the toothed structure of the rail system 10. The gear rotates to drive the light/radiation source carrier 40 to move relative to the rail system 10; hence, the light/radiation source carrier 40 moves along the rail of the rail system 10. This embodiment of the present invention is illustrative rather than restrictive of the power source and the transmission device of the light/radiation source carrier 40. Regardless of its form, the light/radiation source carrier 40 will work, provided that it is capable of moving along the rail of the rail system 10. What is more, the light/radiation source carrier 40 comprises a rotating mechanism $R_S$ and a moving mechanism $M_S$. The rotating mechanism $R_S$ drives the light/radiation source carrier 40 to rotate about an axis $a_{40}$ thereof. The axis $a_{40}$ of the light/radiation source carrier 40 is perpendicular to the reference plane P. The rotating mechanism $R_S$ of the light/radiation source carrier 40 is similar to the rotating mechanism $R_O$ of the object carrier 30 in terms of structure and operation. In this embodiment, the ultimate purpose of the rotating mechanism $R_S$ is to effect the rotation of the light/radiation source S about the axis $a_{40}$ of the light/radiation source carrier 40. The moving mechanism $M_S$ of the light/radiation source carrier 40 drives the light/radiation source S to undergo translation across the reference plane P or across a plane parallel to the reference plane P. The translation includes either a combination of radial translation and tangential translation or just radial translation.

The moving mechanism $M_S$ further comprises a radial moving mechanism $M_{SR}$ and a tangential moving mechanism $M_{ST}$. The radial moving mechanism $M_{SR}$ runs in the radial direction $d_R$ of the rail system 10 to enable the light/radiation source carrier 40 to undergo radial movement. The tangential moving mechanism $M_{ST}$ runs in the tangential direction $d_T$ of the rail system 10 to enable the light/radiation source carrier 40 to undergo tangential movement. The tangential moving mechanism $M_{ST}$ is power-driven or hand-manipulated. The radial moving mechanism $M_{SR}$ and the tangential moving mechanism $M_{ST}$ operate independently of each other.

The detector carrier 50 carries the detector D and is movably disposed at the rail system 10. The detector carrier 50 comprises a power source and a transmission device (such as a stepper motor and a translation device) for driving a driving gear. The driving gear meshes with the toothed structure of the rail system 10. The rotation of the driving gear drives the detector carrier 50 to move relative to the rail system 10. Hence, the detector carrier 50 moves along the rail of the rail system 10. What is more, the detector carrier 50 comprises a rotating mechanism $R_D$ and a moving mechanism $M_D$. The rotating mechanism $R_D$ drives the detector carrier 50 to rotate about an axis $a_{50}$ thereof. The axis $a_{50}$ of the detector carrier 50 is perpendicular to the reference plane P. The rotating mechanism $R_D$ of the detector carrier 50 is similar to the rotating mechanism $R_O$ of the object carrier 30 in terms of structure and operation. In this embodiment, the ultimate purpose of the rotating mechanism $R_D$ is to effect the rotation of the detector D about the axis $a_{50}$. The moving mechanism $M_D$ of the detector carrier 50 drives the detector D to undergo translation across the reference plane P or across a plane parallel to the reference plane P. The translation includes either a combination of radial translation and tangential translation or just radial translation. The moving mechanism $M_D$ of the detector carrier 50 is similar to the moving mechanism $M_S$ of the light/radiation source carrier 40 in terms of structure and operation.

Moreover, the object carrier 30, the light/radiation source carrier 40, and the detector carrier 50 each comprise a height adjusting mechanism H. The height adjusting mechanisms H enable the object carrier 30, the light/radiation source carrier 40, and the detector carrier 50 to undergo height adjustment in a height adjustment direction $d_H$ parallel to the axis $a_{30}$, the axis $a_{40}$, and the axis $a_{50}$, respectively. In practice, to suit all possible scanning needs, a variant embodiment of the present invention is provided and characterized in that the disposition of the height adjusting mechanisms H in the object carrier 30, the light/radiation source carrier 40 and the detector carrier 50 is optional in the sense that it is practicable for at least one, rather than each, of the object carrier 30, the light/radiation source carrier 40 and the detector carrier 50 to be equipped with a said height adjusting mechanism H. The height adjusting mechanisms H are power-driven or hand-manipulated in performing height adjustment, but the present invention is not limited thereto.

The control module 60 has signal communication with the light/radiation source carrier 40 and the detector carrier 50 and adapted to control the light/radiation source carrier 40 and the detector carrier 50, such that the light/radiation source S irradiates the object under test O in accordance with a pre-configured scanning mode selected by a user, and the detector D retrieves projection-related data of the object under test O. In another embodiment, the control module 60 has signal communication with the object carrier 30, the light/radiation source carrier 40 and the detector carrier 50 and adapted to control the object carrier 30, the light/radiation source carrier 40 and the detector carrier 50, so as to allow the light/radiation source S to irradiate the object under test O in accordance with a pre-configured scanning mode selected by the user, allow the detector D to retrieve projection-related data of the object under test O, and allow for more possible scanning modes than it does in the preceding embodiment in which the control module 60 has signal communication with the light/radiation source carrier 40 and the detector carrier 50 only and adapted to control the light/radiation source carrier 40 and the detector carrier 50 only. The control module 60 has RF wireless communication, Wi-Fi wireless communication, or Bluetooth wireless communication with the object carrier 30, the light/radiation source carrier 40 and the detector carrier 50 so as to control the object carrier 30, the light/radiation source carrier 40 and the detector carrier 50, as shown in FIG. 1. Alternatively, a means of cable communication (not shown) substitutes for the aforesaid RF wireless communication, Wi-Fi wireless communication, or Bluetooth wireless communication and still enables the control module 60 to control the object carrier 30, the light/radiation source carrier 40 and the detector carrier 50.

The processing module 70 accesses, by signal communication, the projection-related data retrieved by and stored in the detector D during the scanning process performed according to the pre-configured scanning mode selected by the user. In this embodiment, the signal communication between the processing module 70 and the detector D is exemplified by RF wireless communication, Wi-Fi wireless communication, or Bluetooth wireless communication, as shown in FIG. 1.

Figure 3:
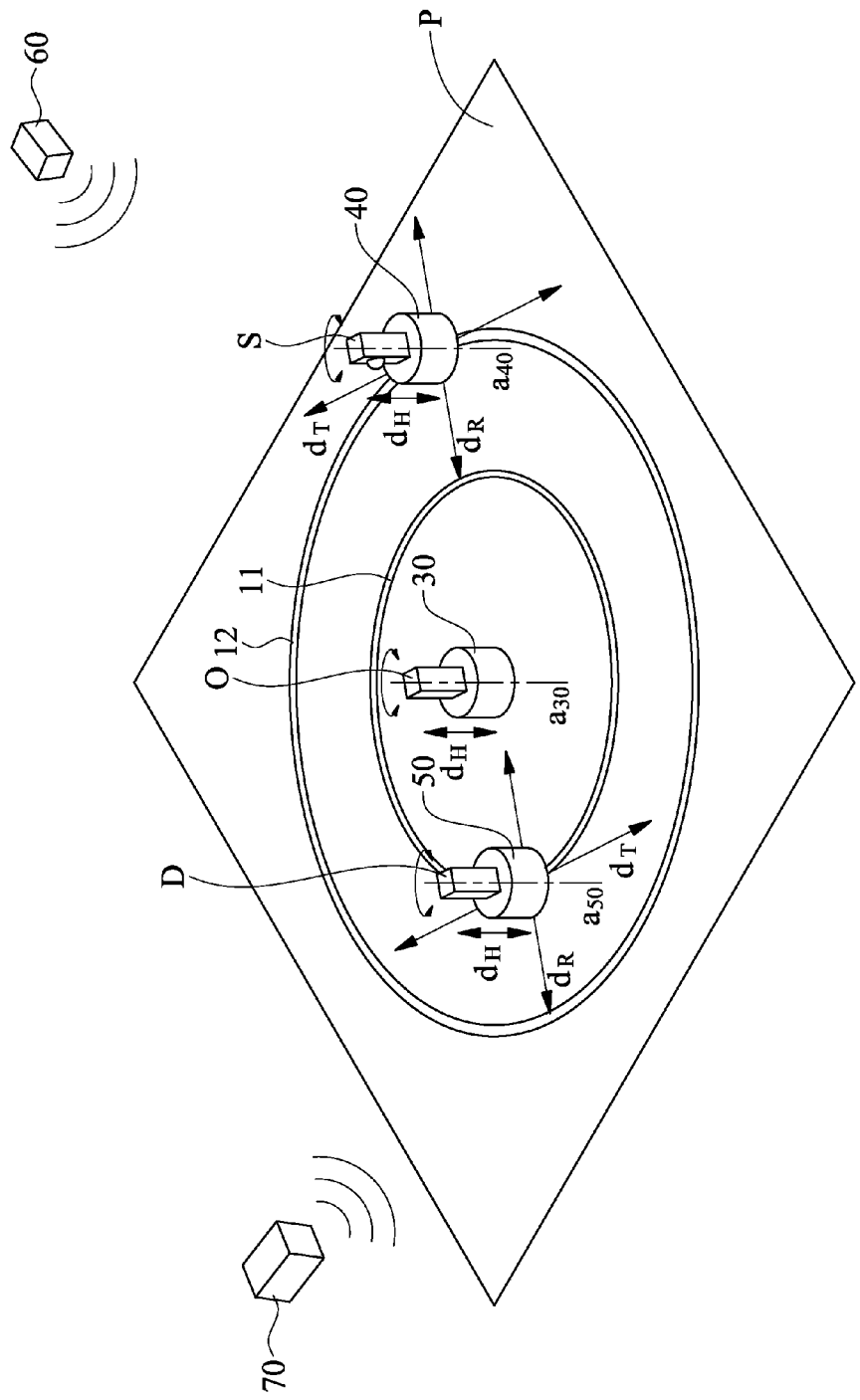
FIG. 3 is a schematic view of the tomographic scanning apparatus according to the second embodiment of the present invention.

Referring to FIG. 3, there is shown a schematic view of the tomographic scanning apparatus 1' according to the second embodiment of the present invention. The tomographic scanning apparatus 1' in the second embodiment is substantially similar to the tomographic scanning apparatus 1 in the first embodiment in terms of structure and operation, except for the number of the rails of the rail system 10 as well as the relationship between the light/radiation source carrier 40 and the detector carrier 50. The aforesaid differences between the first embodiment and the second embodiment are contrasted and compared below.

In the first embodiment, the rail system 10 comprises a closed rail, whereas the light/radiation source carrier 40 and the detector carrier 50 are disposed at the closed rail. Hence, the light/radiation source carrier 40 and the detector carrier 50 move exactly along the same closed rail.

In the second embodiment, the rail system 10 comprises two closed rails, namely a first closed rail 11 and a second closed rail 12, wherein the second closed rail 12 encloses the first closed rail 11. Hence, the first closed rail 11 and the second closed rail 12 are concentric, wherein the light/radiation source carrier 40 and the detector carrier 50 are movably disposed at two different closed rails, respectively. In this embodiment, the light/radiation source carrier 40 moves along the first closed rail 11, and the detector carrier 50 moves along the second closed rail 12. Alternatively, it is also practicable that the light/radiation source carrier 40 moves along the second closed rail 12, and the detector carrier 50 moves along the first closed rail 11.

Figure 4:
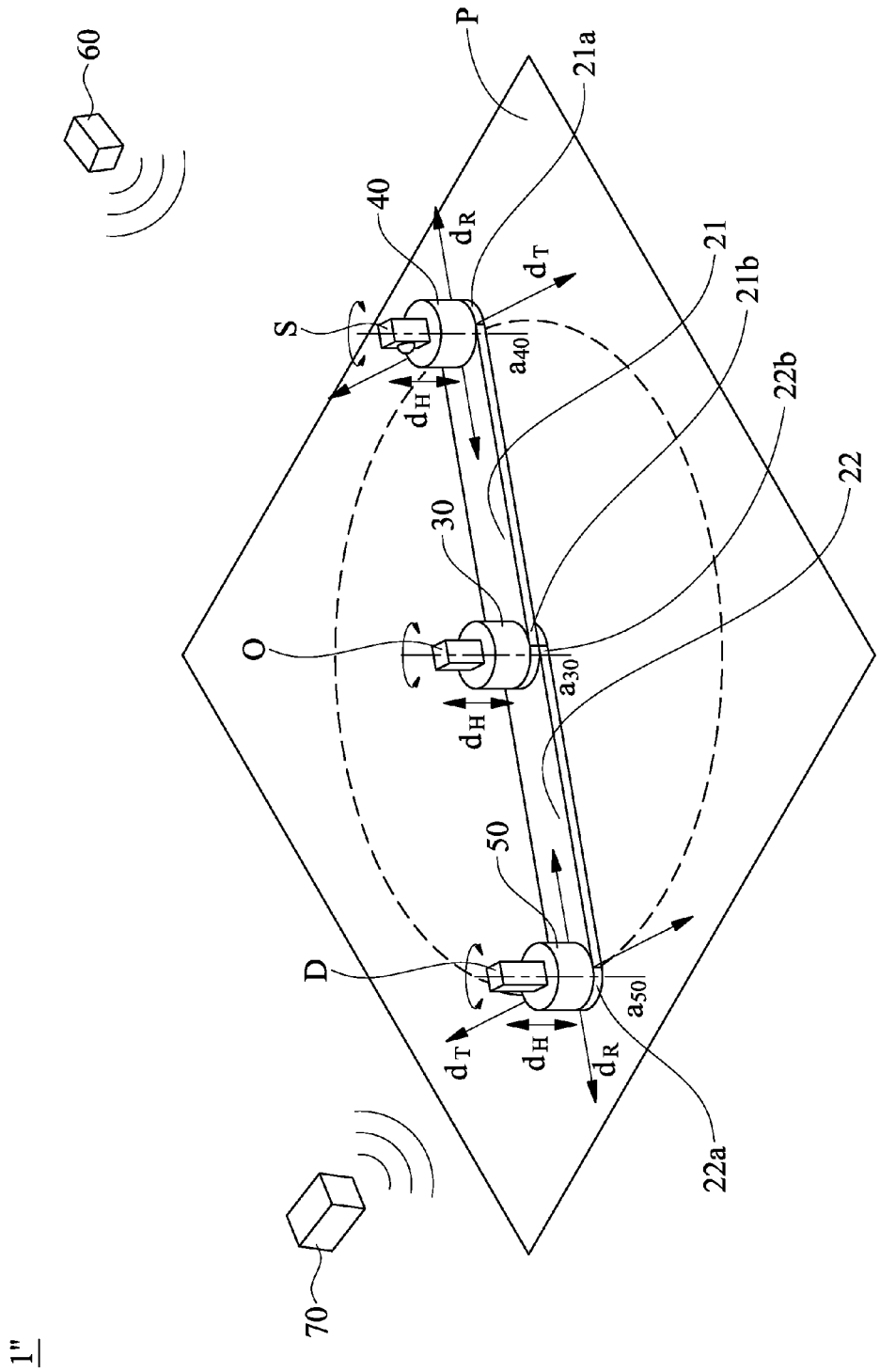
FIG. 4 is a schematic view of a tomographic scanning apparatus according to the third embodiment of the present invention.

Referring to FIG. 4, there is shown a schematic view of a tomographic scanning apparatus 1″ according to the third embodiment of the present invention. The tomographic scanning apparatus 1″ is equipped with a light/radiation source S for scanning an object under test O and equipped with a detector D for retrieving projection-related data of the object under test O. The light/radiation source S emits X-ray, gamma ray, a visible light beam, or a laser light beam. The tomographic scanning apparatus 1″ comprises an object carrier 30, a first rotating arm 21, a second rotating arm 22, a light/radiation source carrier 40, a detector carrier 50, a control module 60, and a processing module 70.

The object carrier 30 lies on the reference plane P and carries the object under test O. The object carrier 30 has signal communication with the control module 60. The object carrier 30 comprises a rotating mechanism $R_O$ (not shown). The rotating mechanism $R_O$ of the object carrier 30 is provided in the form of a direct drive motor for driving the object carrier 30 to rotate about the axis $a_{30}$ thereof under the control of the control module 60 having signal communication with the object carrier 30. The axis $a_{30}$ is perpendicular to the reference plane P. In this embodiment, the ultimate purpose of the rotating mechanism $R_O$ of the object carrier 30 is to drive the object under test O to rotate.

The first rotating arm 21 comprises a first carrying mechanism 21a and a first rotating mechanism 21b. The first rotating mechanism 21b is disposed at one end of the first rotating arm 21, and the object carrier 30 is mounted on the first rotating mechanism 21b. The first rotating mechanism 21b drives the first rotating arm 21 to rotate about the object carrier 30. The first carrying mechanism 21a is disposed at the other end, i.e., the free end, of the first rotating arm 21. The light/radiation source carrier 40, which carries the light/radiation source S, is disposed at the free end of the first rotating arm 21. Hence, the light/radiation source S rotates about the object carrier 30. In a variant embodiment derived from the third embodiment, a rail which runs annularly is disposed around the object carrier 30. The rail and the object carrier 30 are concentric. The first rotating mechanism 21b of the first rotating arm 21 is movably disposed at the rail in a manner that the first rotating arm 21 rotates steadily about the object carrier 30 while being guided by the rail. Hence, the light/radiation source S rotates steadily about the object carrier 30.

The second rotating arm 22 comprises a second carrying mechanism 22a and a second rotating mechanism 22b. The second rotating mechanism 22b is disposed at one end of the second rotating arm 22, and the object carrier 30 is mounted on the second rotating mechanism 22b. The second rotating mechanism 22b drives the second rotating arm 22 to rotate about the object carrier 30. The second carrying mechanism 22a is disposed at the other end, i.e., the free end, of the second rotating arm 22. The detector carrier 50, which carries the detector D, is disposed at the free end of the second rotating arm 22. Hence, the detector D rotates about the object carrier 30. In another variant embodiment derived from the third embodiment, a rail which runs annularly is disposed around the object carrier 30. The rail and the object carrier 30 are concentric. The second rotating mechanism 22b of the second rotating arm 22 is movably disposed at the rail in a manner that the second rotating arm 22 rotates steadily about the object carrier 30 while being guided by the rail. Hence, the detector D rotates steadily about the object carrier 30. In the third embodiment, the first rotating arm 21 is of the same length as the second rotating arm 22, and thus the light/radiation source S follows exactly the same circular path as the detector D does.

The light/radiation source carrier 40 comprises a rotating mechanism $R_S$ and a moving mechanism $M_S$. The rotating mechanism $R_S$ of the light/radiation source carrier 40 is provided in the form of a direct drive motor for driving the light/radiation source carrier 40 to rotate about the axis $a_{40}$ thereof. The moving mechanism $M_S$ of the light/radiation source carrier 40 drives the light/radiation source S to undergo translation across the reference plane P or across a plane parallel to the reference plane P. The translation includes either a combination of radial translation and tangential translation or just radial translation.

The detector carrier 50 carries the detector D and is disposed at a second carrying mechanism 22a of the second rotating arm 22. The detector carrier 50 comprises a rotating mechanism $R_D$ and a moving mechanism $M_D$. The rotating mechanism $R_D$ of the detector carrier 50 is exemplified by a direct drive motor for driving the detector D to rotate about the axis $a_{50}$. The moving mechanism $M_D$ of the detector carrier 50 drives the detector D to undergo translation across the reference plane P or across a plane parallel to the reference plane P. The translation includes either a combination of radial translation and tangential translation or just radial translation.

Moreover, the object carrier 30 comprises a height adjusting mechanism H whereby the object under test O undergoes height adjustment in the height adjustment direction $d_H$ parallel to the axis $a_{30}$ of the object carrier 30, the light/radiation source carrier 40 comprises a height adjusting mechanism H whereby the light/radiation source S undergoes height adjustment in the height adjustment direction $d_H$ parallel to the axis $a_{40}$ of the light/radiation source carrier 40, and/or the detector carrier 50 comprises a height adjusting mechanism H whereby the detector D undergoes height adjustment in the height adjustment direction $d_H$ parallel to the axis $a_{50}$ of the detector carrier 50. The height adjusting mechanism H is power-driven or hand-manipulated. To meet all possible scanning needs, it is preferably that the object carrier 30, the light/radiation source carrier 40 and the detector carrier 50 each comprise the height adjusting mechanism H.

The control module 60 has signal communication with the light/radiation source carrier 40, the detector carrier 50, the first rotating arm 21 and the second rotating arm 22, so as to control the operation of the light/radiation source carrier 40, the detector carrier 50, the first rotating arm 21 and the second rotating arm 22 according to a pre-configured scanning mode selected by the user, such that the light/radiation source S irradiates the object under test O according to the pre-configured scanning mode selected by the user and the detector D retrieves projection-related data of the object under test O according to the pre-configured scanning mode selected by the user. In another embodiment, the control module 60 has signal communication with the object carrier 30, the light/ radiation source carrier 40, the detector carrier 50, the first rotating arm 21 and the second rotating arm 22, so as to control the operation of the object carrier 30, the light/radiation source carrier 40, the detector carrier 50, the first rotating arm 21 and the second rotating arm 22, thereby allowing the light/radiation source S to irradiate the object under test O according to a pre-configured scanning mode selected by the user, allowing the detector D to retrieve projection-related data of the object under test O according to the pre-configured scanning mode selected by the user, and allowing for more possible scanning modes than it does in the preceding embodiment in which the control module 60 has signal communication with the light/radiation source carrier 40, the detector carrier 50, the first rotating arm 21 and the second rotating arm 22 but does not have signal communication with the object carrier 30.

The processing module 70 has signal communication with the detector D, so as to access the projection-related data retrieved by and stored in the detector D.

Figure 5:
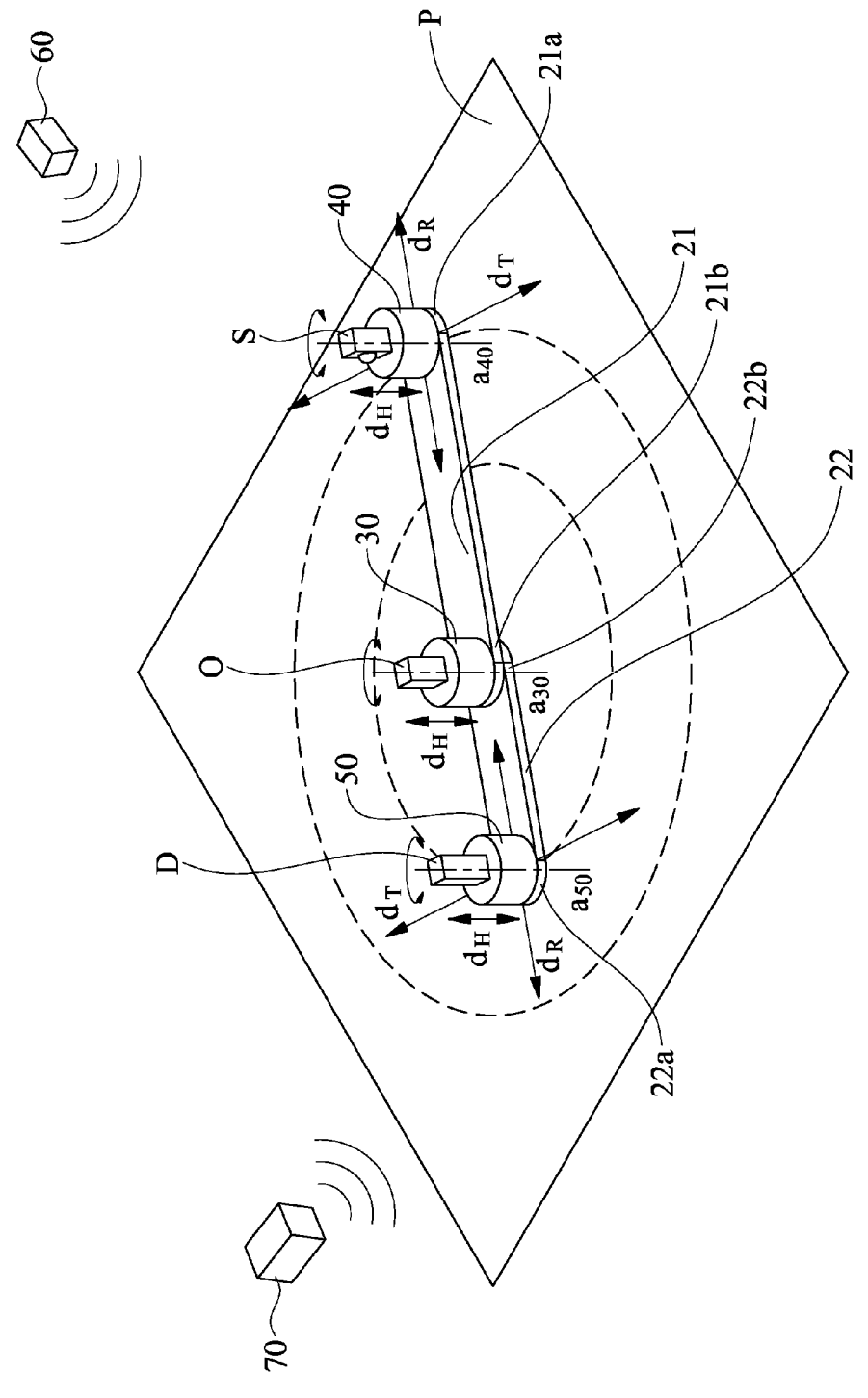
FIG. 5 is a schematic view of the tomographic scanning apparatus according to the fourth embodiment of the present invention.

Referring to FIG. 5, there is shown a schematic view of the tomographic scanning apparatus 1''' according to the fourth embodiment of the present invention. The tomographic scanning apparatus 1''' in the fourth embodiment is substantially similar to the tomographic scanning apparatus 1'' in the third embodiment in terms of constituent elements and operation, except that the first rotating arm 21 and the second rotating arm 22 in the fourth embodiment are of different lengths, whereas the first rotating arm 21 and the second rotating arm 22 in the third embodiment are of equal lengths. The aforesaid differences and their resultant effects are further explained below.

In the third embodiment, the first rotating arm 21 and the second rotating arm 22 are of equal lengths. The light/radiation source carrier 40 and the detector carrier 50 are disposed at the first rotating arm 21 and the second rotating arm 22, respectively. Alternatively, the light/radiation source carrier 40 and the detector carrier 50 are disposed at the second rotating arm 22 and the first rotating arm 21, respectively. As the first rotating arm 21 and the second rotating arm 22 are of equal lengths, the light/radiation source carrier 40 and the detector carrier 50 follow the same rotation path.

In the fourth embodiment, the first rotating arm 21 and the second rotating arm 22 are of different lengths. The light/radiation source carrier 40 and the detector carrier 50 are disposed at the first rotating arm 21 and the second rotating arm 22, respectively. Alternatively, the light/radiation source carrier 40 and the detector carrier 50 are disposed at the second rotating arm 22 and the first rotating arm 21, respectively. As the first rotating arm 21 and the second rotating arm 22 are of different lengths, the light/radiation source carrier 40 and the detector carrier 50 follow two concentric rotation paths, respectively.

The above embodiments illustrate the constituent elements and operation of the tomographic scanning apparatuses of the present invention. The coordination and combinations of the constituent elements of the tomographic scanning apparatuses operating in different illustrative scanning modes are depicted in FIGS. 6A-6E, exemplified by the first embodiment, and described below.

Figure 6A:
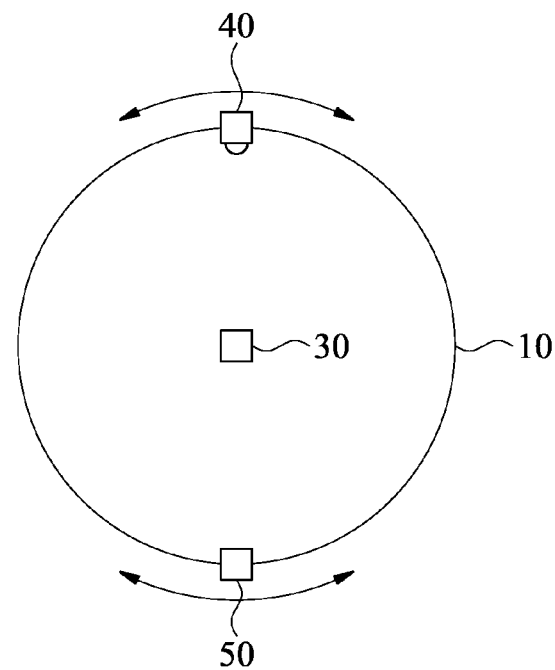
FIGS. 6A-6E are schematic views of different scanning modes according to the present invention.
Figure 6A:
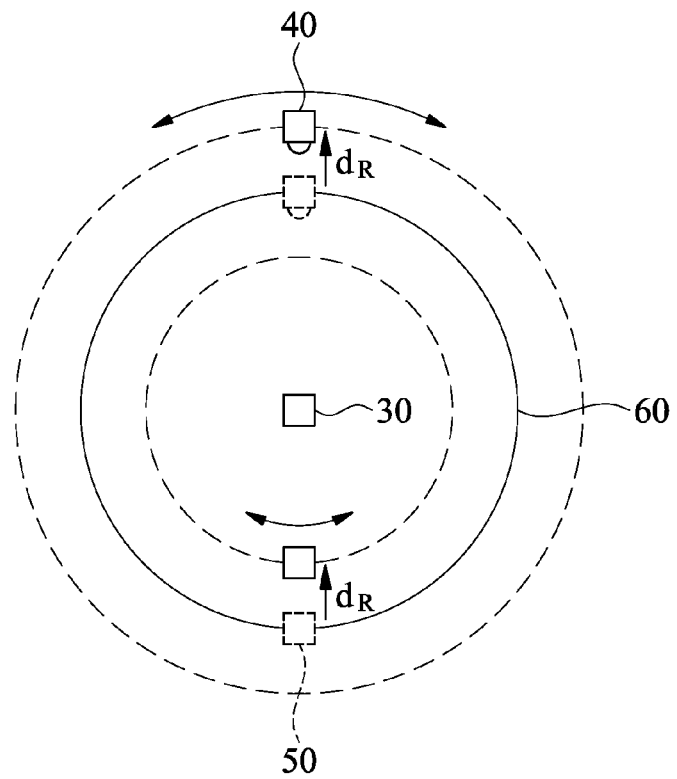

Referring to FIG. 6A, there is shown a schematic view of the scanning mode referred to briefly as "light/radiation source and detector" which is applicable to dental tomographic scanning apparatuses. The scanning mode comprises the steps of: (1) adjusting the height and translation, by the control module 60 in a power-driven or hand-manipulated manner, of the object carrier 30 for carrying the object under test O, the light/radiation source carrier 40 for carrying the light/radiation source S, the height adjusting mechanism H of the detector carrier 50 of the detector D, until the object under test O, the light/radiation source S and the detector D are positioned appropriately, for example, lying on the same plane and being collinear, thereby allowing the detector D to retrieve the projection-related data of the object under test O; (2) control the light/radiation source carrier 40 and the detector carrier 50 to move along the closed rail of the rail system 10 (see the top diagram of FIG. 6A), or adjusting the distance between the radial moving mechanism $M_{SR}$ and the axis a30 and the distance between the radial moving mechanism $M_{DR}$ and the axis a30 (see the bottom diagram of FIG. 6A), wherein the scanning process takes place only when the light/radiation source carrier 40 and the detector carrier 50 are opposite to each other, that is, the scanning process takes place only at the point in time when the linear distance between the light/radiation source carrier 40 and the detector carrier 50 is at its maximum; (3) generating X-ray, gamma ray, visible light, or a laser light beam from the light/radiation source S, such that the X-ray, gamma ray, visible light, or the laser light beam penetrates the object under test O before reaching the detector D, so as for the detector D to detect the X-ray, gamma ray, visible light, or the laser light beam and retrieve projection-related data of the object under test O accordingly, and so as for the processing module 70 to process the projection-related data attributed to the object under test O and retrieved by the detector D; and (4) repeating step (2) and step (3) to obtain the projection-related data retrieved by the detect D from different angles of view. In step (2) and step (3), if the height adjusting mechanism H of the object carrier 30 is in operation to elevate or lower the object under test O gradually, a scanning effect known as "spiral computer tomographic scanning" will be achieved. The above steps and their sequence are illustrative rather than restrictive of the present invention; for example, if, prior to a scan, the object under test O, the light/radiation source S, and the detector D are positioned in place, then step (1) can be left out.

Figure 6B:
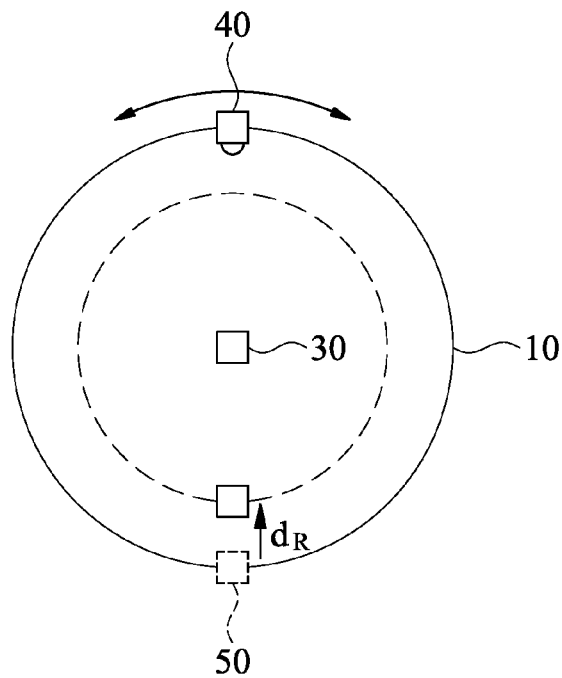

Referring to FIG. 6B, there is shown a schematic view of the scanning mode referred to briefly as "stationary detector, rotatable light/radiation source". The scanning mode is applicable to mammo-tomographic scanning. The scanning mode comprises the steps of: (1) adjusting the height of the height adjusting mechanisms H of the object carrier 30, the light/radiation source carrier 40 and the detector carrier 50, controlling the translation of the tangential moving mechanism $M_{ST}$ of the light/radiation source carrier 40, and controlling the translation of the tangential moving mechanism $M_{DT}$ of the detector carrier 50 by the control module 60 in a power-driven or hand-manipulated manner, until the object under test O, the light/radiation source S and the detector D are positioned appropriately, for example, lying on the same, thereby allowing the detector D to retrieve the projection-related data of the object under test O; (2) adjusting the distance between the radial moving mechanism $M_{DR}$ of the detector carrier 50 and the axis a30 ; (3) controlling the light/radiation source carrier 40 to move along the closed rail of the rail system 10; (4) generating X-ray, gamma ray, visible light, or a laser light beam from the light/radiation source S, such that the X-ray, gamma ray, visible light, or the laser light beam penetrates the object under test O before reaching the detector D, so as for the detector D to detect the X-ray, gamma ray, visible light, or the laser light beam and retrieve projection-related data of the object under test O accordingly, and so as for the processing module 70 to process the projection-related data attributed to the object under test O and retrieved by the detector D; and (5) repeating step (3) and step (4) to obtain the projection-related data retrieved by the detect D from different angles of view. The above steps and their sequence are illustrative rather than restrictive of the present invention; for example, if, prior to a scan, the object under test O, the light/radiation source S, and the detector D are positioned in place, then step (1) can be left out.

Figure 6C:
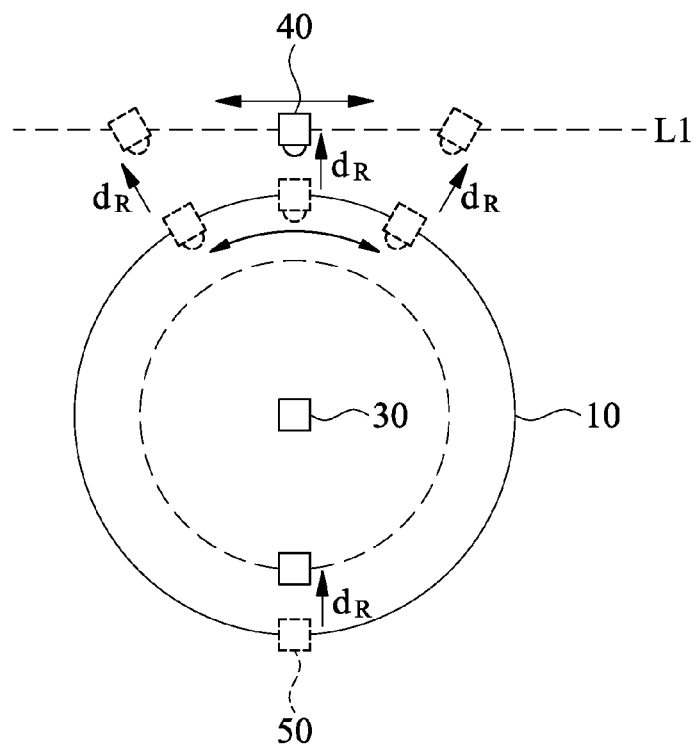

Referring to FIG. 6C, there is shown a schematic view of the scanning mode referred to briefly as "stationary detector, linearly-moving light/radiation source". The scanning mode is applicable to vertical thoracic synthesized tomography scanning. The scanning mode comprises the steps of: (1) adjusting the height, by the control module 60 in a power-driven or hand-manipulated manner, of the height adjusting mechanisms H of the object carrier 30, the light/radiation source carrier 40 and the detector carrier 50, controlling the translation of the tangential moving mechanism $M_{ST}$ of the light/radiation source carrier 40, controlling the translation of the tangential moving mechanism $M_{DT}$ of the detector carrier 50, until the object under test O, the light/radiation source S and the detector D are positioned appropriately, for example, lying on the same plane, thereby allowing the detector D to retrieve the projection-related data of the object under test O; (2) adjusting the distance between the radial moving mechanism $M_{DR}$ of the detector carrier 50 and the axis $a_{30}$; (3) controlling the translation of the radial moving mechanism $M_{SR}$ of the light/radiation source carrier 40 while the light/radiation source carrier 40 is moving along a specific segment of the rail of the rail system 10 such that the light/radiation source carrier 40 always lies on a straight line L1; (4) controlling the rotating mechanism $R_S$ of the light/radiation source carrier 40, such that the light/radiation source S always points at the detector D, thereby allowing the detector D to retrieve the projection-related data of the object under test O; (5) generating X-ray, gamma ray, visible light, or a laser light beam from the light/radiation source S, such that the X-ray, gamma ray, visible light, or the laser light beam penetrates the object under test O before reaching the detector D, so as for the detector D to detect the X-ray, gamma ray, visible light, or the laser light beam and retrieve projection-related data of the object under test O accordingly, and so as for the processing module 70 to process the projection-related data attributed to the object under test O and retrieved by the detector D; and (6) repeating step (3) through step (5), so as to obtain the projection-related data retrieved by the detector D from different angles of view. The above steps and their sequence are illustrative rather than restrictive of the present invention; for example, if, prior to a scan, the object under test O, the light/radiation source S, and the detector D are positioned in place, then step (1) can be left out.

Figure 6D:
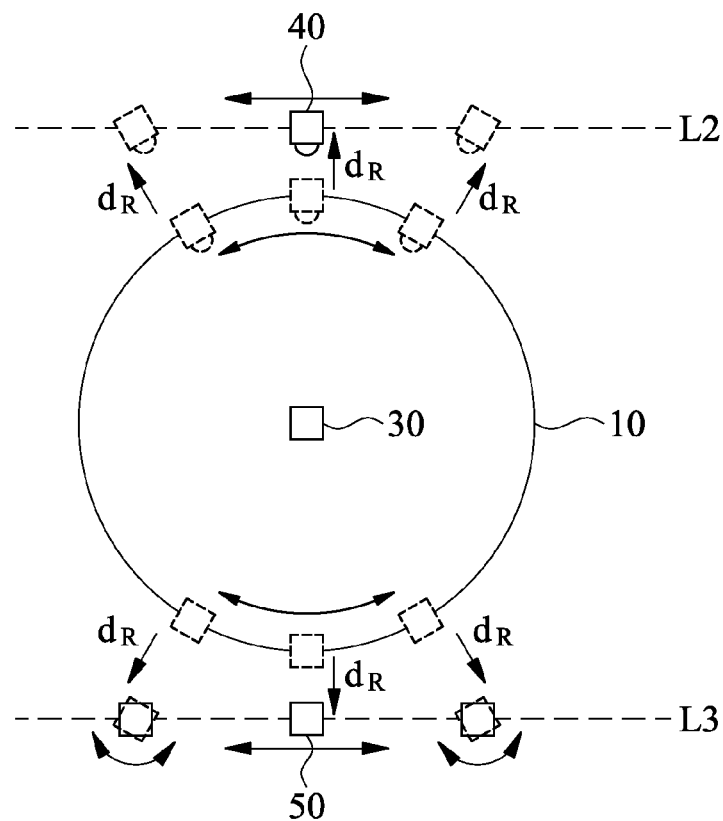

Referring to FIG. 6D, there is shown a schematic view of the scanning mode referred to briefly as "light/radiation source and detector moving linearly relative to each other". The scanning mode is applicable to platform synthesized tomography scanning. The scanning mode comprises the steps of: (1) adjusting the height of the height adjusting mechanisms H of the object carrier 30, the light/radiation source carrier 40 and the detector carrier 50, controlling the translation of the tangential moving mechanism $M_{ST}$ of the light/radiation source carrier 40, controlling the translation of the tangential moving mechanism $M_{DT}$ of the detector carrier 50 by the control module 60 in a power-driven or hand-manipulated manner, until the object under test O, the light/radiation source S and the detector D are positioned appropriately, for example, lying on the same plane and being collinear, thereby allowing the detector D to retrieve the projection-related data of the object under test O; (2) controlling the translation of the radial moving mechanism $M_{SR}$ of the light/radiation source carrier 40 while the light/radiation source carrier 40 is moving along a specific segment of the rail of the rail system 10 such that the light/radiation source carrier 40 always lies on a straight line L2; (3) controlling the translation of the radial moving mechanism $M_{DR}$ of the detector carrier 50 while the detector carrier 50 is moving along a specific segment of the rail of the rail system 10 such that the detector carrier 50 always lies on a straight line L3; (4) controlling the rotating mechanism $R_S$ of the light/radiation source carrier 40 such that the light/radiation source S always points at the detector D, and controlling the rotating mechanism $R_D$ of the detector carrier 50 such that the detector O always faces in a direction perpendicular to the line L3, so as to retrieve the projection-related data of the object under test O; (5) generating X-ray, gamma ray, visible light, or a laser light beam from the light/radiation source S, such that the X-ray, gamma ray, visible light, or the laser light beam penetrates the object under test O before reaching the detector D, so as for the detector D to detect the X-ray, gamma ray, visible light, or the laser light beam and retrieve projection-related data of the object under test O accordingly, and so as for the processing module 70 to process the projection-related data attributed to the object under test O and retrieved by the detector D; and (6) repeating step (2) through step (5), so as to obtain the projection-related data retrieved by the detector D from different angles of view. The above steps and their sequence are illustrative rather than restrictive of the present invention; for example, if, prior to a scan, the object under test O, the light/radiation source S, and the detector D are positioned in place, then step (1) can be left out.

Figure 6E:
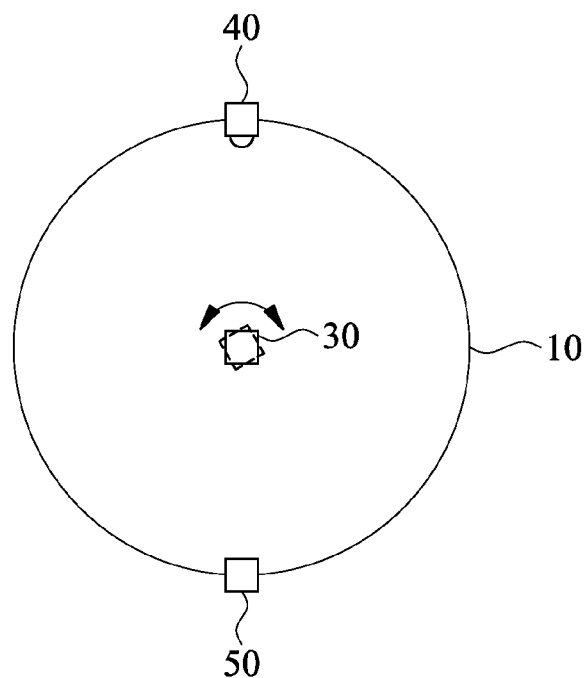

Referring to FIG. 6E, there is shown a schematic view of the scanning mode referred to briefly as "stationary light/radiation source and detector, self-rotating object under test". The scanning mode is applicable to industrial noninvasive testing. The scanning mode comprises the steps of: (1) adjusting the height of the height adjusting mechanisms H of the object carrier 30, the light/radiation source carrier 40 and the detector carrier 50, controlling the translation of the tangential moving mechanism $M_{ST}$ of the light/radiation source carrier 40, and controlling the translation of the tangential moving mechanism $M_{DT}$ of the detector carrier 50 by the control module 60 in a power-driven or hand-manipulated manner; (2) controlling the translation of the moving mechanism $M_S$ of the light/radiation source carrier 40 and controlling the translation of the moving mechanism $M_D$ of the detector carrier 50 so as to change the distance between the light/radiation source carrier 40 and the axis $a_{30}$ and the distance between the detector carrier 50 and the axis $a_{30}$ as appropriate; (3) driving by the rotating mechanism $R_O$ the object carrier 30 to rotate; (4) generating X-ray, gamma ray, visible light, or a laser light beam from the light/radiation source S, such that the X-ray, gamma ray, visible light, or the laser light beam penetrates the object under test O before reaching the detector D, so as for the detector D to detect the X-ray, gamma ray, visible light, or the laser light beam and retrieve projection-related data of the object under test O from different angles of view accordingly, and so as for the processing module 70 to process the projection-related data attributed to the object under test O and retrieved by the detector D. The above steps and their sequence are illustrative rather than restrictive of the present invention; for example, if, prior to a scan, the object under test O, the light/radiation source S, and the detector D are positioned in place, then step (1) can be left out.

The projection-related data attributed to the object under test O and retrieved according to the aforesaid scanning mode from different angles of view undergo image reconstruction with an external image reconstructing and processing unit or a built-in image reconstructing and processing unit of the tomographic scanning apparatus, so as to produce tomographic images of the object under test O The aforesaid scanning modes, which are illustrative rather than restrictive of the tomographic scanning apparatus of the present invention, allow persons skilled in the art to gain insight into the way the moving mechanisms are disposed and altered to meet the needs of the scanning mode. Persons skilled in the art understand that the tomographic scanning apparatus is not limited to the aforesaid purposes and operation, and that the tomographic scanning apparatus meets a wide variety of scanning needs.

The tomographic scanning apparatus of the present invention is not only characterized by multiple scanning modes but is also applicable to the research and development (R&D) of an imaging apparatus. Prior to its design state, a conventional imaging apparatus must have its dimensions, size, relative positions of constituent components, parameters of the scanning modes roughly determined. During its design state, the conventional imaging apparatus must have its dimensions, size, relative positions of constituent components, parameters of the scanning modes adjusted from time to time as needed. On the contrary, relative positions of constituent components and parameters of the scanning modes of the tomographic scanning apparatus of the present invention are adjustable during operation advantageously as needed rather than during design state, thereby dispensing with the hassle of performing re-design of the hardware mechanisms of the conventional imaging apparatus during the design state at a discouragingly huge amount of costs.

The tomographic scanning apparatus of the present invention is characterized by multiple scanning modes which is conducive to the enhancement of the industrial applicability of the tomographic scanning apparatus and minimizes the likelihood of tremendous changes and redesign.

The present invention is disclosed above by preferred embodiments. However, persons skilled in the art should understand that the preferred embodiments are illustrative of the present invention only, but should not be interpreted as restrictive of the scope of the present invention. Hence, all equivalent modifications and replacements made to the aforesaid embodiments should fall within the scope of the present invention. Accordingly, the legal protection for the present invention should be defined by the appended claims.

What is claimed is:

1. A tomographic scanning apparatus, having a light/radiation source for scanning an object under test and a detector for retrieving projection-related data of the object under test, comprising:
   a rail system lying on a reference plane;
   an object carrier adapted to carry the object under test and disposed at a center of the rail system;
   a light/radiation source carrier adapted to carry the light/radiation source, movably disposed at the rail system, and comprising a rotating mechanism and a moving mechanism, the rotating mechanism driving the light/radiation source to rotate about an axis of the light/radiation source carrier, the axis being perpendicular to the reference plane, and the moving mechanism driving the light/radiation source to undergo translation across the reference plane or across a plane parallel to the reference plane;
   a detector carrier adapted to carry the detector, movably disposed at the rail system, and comprising a rotating mechanism and a moving mechanism, the rotating mechanism driving the detector to rotate about an axis of the detector carrier, and the moving mechanism driving the detector to undergo translation across the reference plane or across a plane parallel to the reference plane;
   a control module having signal communication with the light/radiation source carrier and the detector carrier to control operation of the light/radiation source carrier and the detector carrier according to a pre-configured scanning mode, thereby allowing the light/radiation source to irradiate the object under test according to the pre-configured scanning mode, and allowing the detector to retrieve projection-related data of the object under test according to the pre-configured scanning mode; and
   a processing module having signal communication with the detector to access the projection-related data retrieved by the detector.

2. The tomographic scanning apparatus of claim 1, wherein the object carrier has signal communication with the control module and comprises a rotating mechanism for driving the object under test to rotate about an axis of the object carrier.

3. The tomographic scanning apparatus of claim 2, wherein the object carrier comprises a height adjusting mechanism whereby the object under test undergoes height adjustment in a direction parallel to the axis of the object carrier, the light/radiation source carrier comprises a height adjusting mechanism whereby the light/radiation source undergoes height adjustment in a direction parallel to the axis of the light/radiation source carrier, and/or the detector carrier comprises a height adjusting mechanism whereby the detector undergoes height adjustment in a direction parallel to the axis of the detector carrier.

4. The tomographic scanning apparatus of claim 3, wherein the rail system comprises a closed rail on which the light/radiation source carrier and the detector carrier are movably disposed.

5. The tomographic scanning apparatus of claim 3, wherein the rail system comprises:
   a first closed rail; and
   a second closed rail enclosing the first closed rail;
   wherein the light/radiation source carrier is disposed at one of the first and second closed rails, and the detector carrier is disposed at another one of the first and second closed rails.

6. The tomographic scanning apparatus of claim 2, wherein the rail system comprises a closed rail, such that the light/radiation source carrier and the detector carrier are movably disposed at the closed rail.

7. The tomographic scanning apparatus of claim 2, wherein the rail system comprises:
   a first closed rail; and
   a second closed rail enclosing the first closed rail;
   wherein the light/radiation source carrier is disposed at one of the first and second closed rails, and the detector carrier is disposed at another one of the first and second closed rails.

8. The tomographic scanning apparatus of claim 1, wherein the object carrier has signal communication with the control module and includes a height adjusting mechanism whereby the object under test undergoes height adjustment in a height adjustment direction parallel to an axis of the object carrier, the light/radiation source carrier has signal communication with the control module and includes a height adjusting mechanism whereby the light/radiation source undergoes height adjustment in a height adjustment direction parallel to an axis of the light/radiation source carrier, and/or the detector carrier has signal communication with the control module and includes a height adjusting mechanism whereby the detector undergoes height adjustment in a height adjustment direction parallel to an axis of the detector carrier.

9. The tomographic scanning apparatus of claim 8, wherein the rail system comprises a closed rail, and the light/radiation source carrier and the detector carrier are movably disposed at the closed rail.

10. The tomographic scanning apparatus of claim 8, wherein the rail system comprises:
a first closed rail; and
a second closed rail enclosing the first closed rail;
wherein the light/radiation source carrier is disposed at one of the first and second closed rails, and the detector carrier is disposed at another one of the first and second closed rails.

11. The tomographic scanning apparatus of claim 1, wherein the rail system comprises a closed rail, such that the light/radiation source carrier and the detector carrier are movably disposed at the closed rail.

12. The tomographic scanning apparatus of claim 1, wherein the rail system comprises:
a first closed rail; and
a second closed rail enclosing the first closed rail;
wherein the light/radiation source carrier is disposed at one of the first and second closed rails, and the detector carrier is disposed at another one of the first and second closed rails.

13. The tomographic scanning apparatus of claim 1, wherein the rail system is one of a circular path and an elliptical path.

14. A tomographic scanning apparatus, having a light/radiation source for scanning an object under test and a detector for retrieving projection-related data of the object under test, comprising:
an object carrier lying on a reference plane and adapted to carry the object under test;
a first rotating arm comprising a first carrying mechanism and a first rotating mechanism, wherein the first rotating mechanism is disposed at an end of the first rotating arm, the object carrier is mounted on the first rotating mechanism, the first rotating mechanism drives the first rotating arm to rotate about an axis of the object carrier, the axis being perpendicular to the reference plane, and the first carrying mechanism is disposed at another end of the first rotating arm;
a second rotating arm comprising a second carrying mechanism and a second rotating mechanism, the second carrying mechanism being disposed at an end of the second rotating arm, and the second rotating mechanism being disposed at another end of the second rotating arm and rotating about the axis of the object carrier;
a light/radiation source carrier adapted to carry the light/radiation source, disposed at the first carrying mechanism of the first rotating arm, and comprising a rotating mechanism and a moving mechanism, the rotating mechanism driving the light/radiation source to rotate about an axis of the light/radiation source carrier, and the moving mechanism driving the light/radiation source to undergo translation across one of the reference plane and a plane parallel to the reference plane;
a detector carrier adapted to carry the detector, disposed at the second carrying mechanism of the second rotating arm, and comprising a rotating mechanism and a moving mechanism, the rotating mechanism driving the detector to rotate about an axis of the detector carrier, and the moving mechanism driving the detector to undergo translation across one of the reference plane and a plane parallel to the reference plane;
a control module having signal communication with the light/radiation source carrier, the detector carrier, the first rotating arm, and the second rotating arm to control the light/radiation source carrier, the detector carrier, the first rotating arm, and the second rotating arm according to a pre-configured scanning mode and thus allow the object under test to be irradiated by the light/radiation source according to the pre-configured scanning mode and allow the detector to retrieve the projection-related data of the object under test according to the pre-configured scanning mode; and
a processing module having signal communication with the detector to access the projection-related data retrieved by the detector.

15. The tomographic scanning apparatus of claim 14, wherein the object carrier has signal communication with the control module and comprises a rotating mechanism for driving the object under test to rotate about an axis of the object carrier.

16. The tomographic scanning apparatus of claim 15, wherein the object carrier includes a height adjusting mechanism whereby the object under test undergoes height adjustment in a height adjustment direction parallel to an axis of the object carrier, the light/radiation source carrier includes a height adjusting mechanism whereby the light/radiation source undergoes height adjustment in a height adjustment direction parallel to an axis of the light/radiation source carrier, and/or the detector carrier includes a height adjusting mechanism whereby the detector undergoes height adjustment in a height adjustment direction parallel to an axis of the detector carrier.

17. The tomographic scanning apparatus of claim 14, wherein the object carrier has signal communication with the control module, the object carrier includes a height adjusting mechanism whereby the object under test undergoes height adjustment in a height adjustment direction parallel to an axis of the object carrier, the light/radiation source carrier includes a height adjusting mechanism whereby the light/radiation source undergoes height adjustment in a height adjustment direction parallel to an axis of the light/radiation source carrier, and/or the detector carrier includes a height adjusting mechanism whereby the detector undergoes height adjustment in a height adjustment direction parallel to an axis of the detector carrier.

18. The tomographic scanning apparatus of claim 14, wherein the first rotating arm and the second rotating arm are of equal lengths.

19. The tomographic scanning apparatus of claim 14, wherein the first rotating arm and the second rotating arm are of different lengths.

* * * * *